US00PP29213P2

(12) United States Plant Patent
Dodd et al.

(10) Patent No.: US PP29,213 P2
(45) Date of Patent: Apr. 10, 2018

(54) APPLE TREE NAMED 'MAIA12'

(50) Latin Name: *Malus×domestica*
Varietal Denomination: MAIA12

(71) Applicants: William Dodd, Newcomerstown, OH (US); David Doud, Wabash, IN (US); John Mitchell Lynd, Pataskala, OH (US); Gregory Miller, Carrollton, OH (US)

(72) Inventors: William Dodd, Newcomerstown, OH (US); David Doud, Wabash, IN (US); John Mitchell Lynd, Pataskala, OH (US); Gregory Miller, Carrollton, OH (US)

(73) Assignee: MIDWEST APPLE IMPROVEMENT ASSOCIATION, Newcomerstown, OH (US)

( * ) Notice: Subject to any disclaimer, the term of this patent is extended or adjusted under 35 U.S.C. 154(b) by 0 days.

(21) Appl. No.: 15/330,375

(22) Filed: Sep. 12, 2016

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

*Primary Examiner* — Kent L Bell
(74) *Attorney, Agent, or Firm* — Flynn, Thiel, Boutell & Tanis, P.C.

(57) ABSTRACT

A new and distinct variety of apple tree was identified from a population of seedlings derived from a cross of 'Honeycrisp' and 'Fuji'. The new variety, named 'MAIA12' is distinct from 'Honeycrisp' as 'MAIA12' ripens late-August, 1 week before 'Honeycrisp'. Unlike 'Honeycrisp', 'MAIA12' is a fast-growing, vigorous tree with long shoots and leaves. 'MAIA12' is distinct from 'Fuji' as 'MAIA12' ripens 6 weeks before 'Fuji'. Unlike 'Fuji', 'MAIA12' has consistent annual cropping with minimal horticultural inputs. 'MAIA12' fruit are medium sized, extremely crisp, with simple sweet-tart flavor and long storability.

2 Drawing Sheets

Latin name of the genus and species of the plant claimed: *Malus×domestica.*

Variety denomination: 'MAIA12'.

BACKGROUND OF THE INVENTION

A new and distinct variety of apple tree was identified from a population of seedlings derived from a cross of 'Honeycrisp' (U.S. Plant Pat. No. 7,197) and 'Fuji' (not patented—original strain originating from a cross of 'Delicious' (not patented) and 'Rails Janet' (not patented) made in Japan and released as a variety in 1962). This cross was made as a part of the Midwest Apple Improvement Association apple-breeding project. This superior seedling tree was identified in a population of seedlings from this cross at Wabash, Ind.

The seedling tree was planted as a 1-year-old tree at Wabash, Ind. in 2001 and grown among a population of several hundred siblings. Evaluations of fruit quality and tree growth parameters were begun in 2005 and this seedling was identified over several years as superior based upon tree growth habit, precocity, superior fruit quality, and harvest time. Utilizing grafting reproduction, the new apple tree variety was asexually propagated by David Doud in 2010 at Wabash, Ind. and has been observed to remain true to the description set forth herein.

The closest comparison variety to 'MAIA12' is 'Honeycrisp'. The new variety 'MAIA12' is distinct from 'Honeycrisp' as 'MAIA12' ripens late-August, 1 week before 'Honeycrisp' (FIG. 1). Unlike 'Honeycrisp', 'MAIA12' is a fast-growing, vigorous tree with long shoots and leaves (FIG. 3). The fruit of 'MAIA12' is a distinctive pink color (Red Group 45A). 'MAIA12' is distinct from 'Fuji' as 'MAIA12' ripens 6 weeks before 'Fuji'. Unlike 'Fuji', 'MAIA12' has consistent annual cropping with minimal horticultural inputs. 'MAIA12' fruit (FIG. 2) are medium sized, extremely crisp, with simple sweet-tart flavor and long storability. Based on tree vigor and consistent annual cropping, the yield potential of 'MAIA12' is higher than either 'Fuji' or 'Honeycrisp'.

BRIEF DESCRIPTION OF THE DRAWINGS

The accompanying photographs show typical specimens of the new variety as depicted in color as nearly true as is reasonably possible. 'MAIA12' photographs were taken in Canfield, Ohio.

DETAILED BOTANICAL DESCRIPTION

Figure 1:
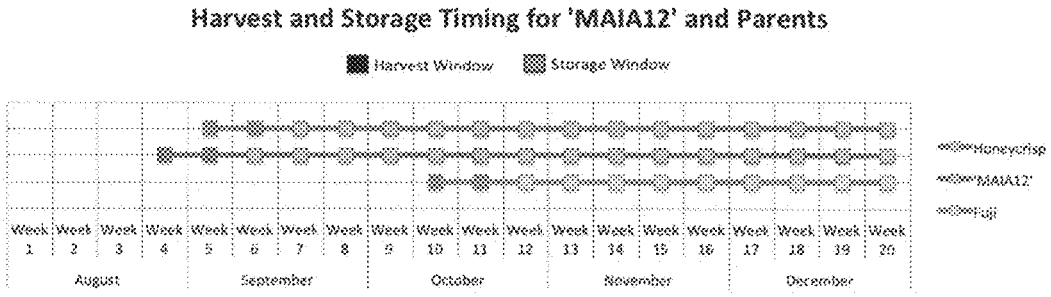
FIG. 1. Shows that 'MAIA12' is distinct from 'Honeycrisp' and 'Fuji' in harvest window.
Figure 2:
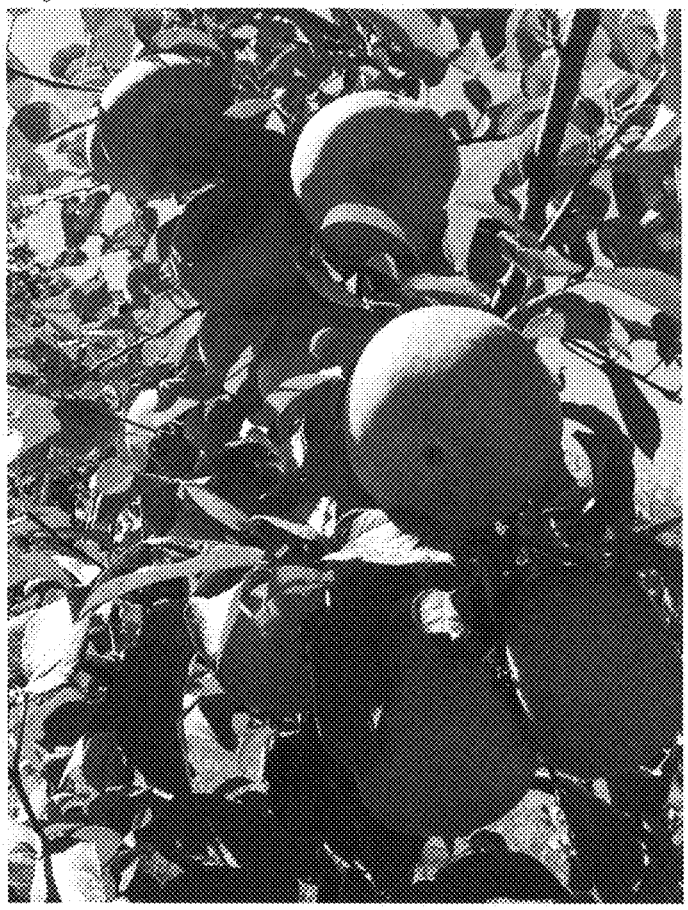
FIG. 2. Typical fruit of 'MAIA12' at harvest time.
Figure 3:
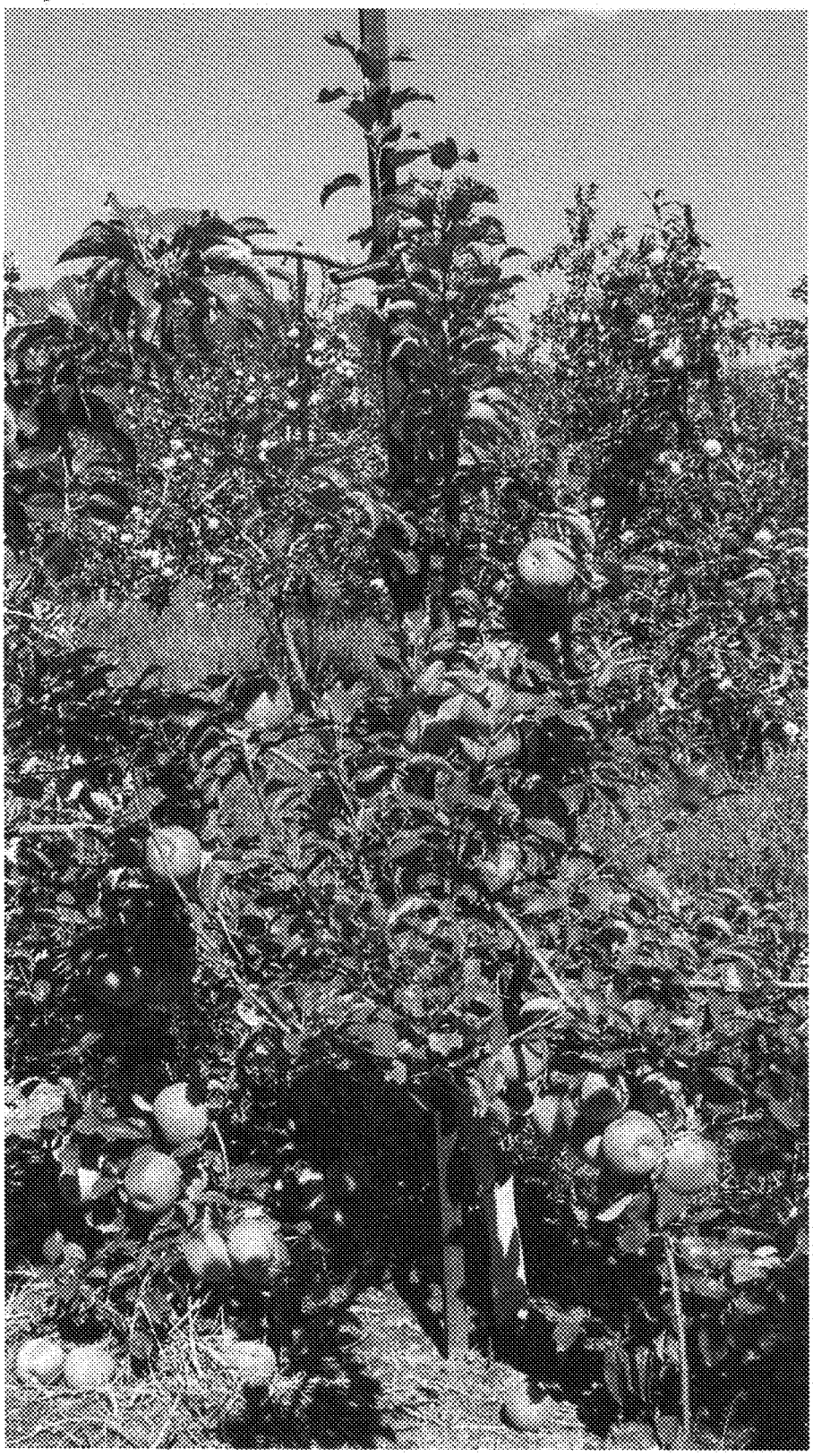
FIG. 3. Typical 'MAIA12' trees bearing fruit in August in Ohio.

Color references are made to The Royal Horticultural Society Colour Chart (R.H.S.) 2001 Edition.

Parentage: 'Honeycrisp' female parent and 'Fuji' male parent; controlled cross made by Greg Miller at Pataskala, Ohio in 1999.

Original seedling tree:

*Age.*—17 years.

*Size.*—15' height, 15' spread.

*Vigor.*—Medium.

*Form*.—Round, spreading.
*Production*.—Very productive.
*Growth type*.—Spindle tree growth form, productive spurs located throughout tree.
*Bearing*.—Annual.

Trunk:
*Original seedling tree size*.—18 cm at 15 cm height.
*Bark color*.—Greyed-Green 197B.
*Lenticel*.—Ovate, 3-4 mm.
*Lenticel color*.—Greyed-Yellow 161B.
*Lenticel density*.—6-12 lenticels/cm$^2$.

Branches:
3 *year old*.—16-22 mm in diameter, branch angle 70-80°; Greyed-Green 197C; typical branch length of 35-50 cm.
2 *year old*.—14-18 mm in diameter, branch angle 70-80°; Grey-Brown N199A; typical branch length of 35-40 cm.
1 *year old*.—9-10 mm in diameter, branch angle 70-80°; Grey-Orange 166A; typical branch length of 25-35 cm.

Leaves:
*Size*.—Length 88-105 mm; width 55-70 mm.
*Texture*.—Leathery, crisp.
*Form*.—Ovate.
*Base*.—Roundly cuneate.
*Apex*.—Acute.
*Adaxial surface pubescence*.—None.
*Abaxial pubescence*.—Lightly pubescent.
*Adaxial surface color*.—Yellow-Green 147A.
*Abaxial surface color*.—Yellow-Green 148B.
*Veination*.—Pinnate, 8-9 major veins, mainly alternate.
*Margin*.—Serrate.
*Petiole length*.—33-36 mm.
*Petiole width*.—2 mm.
*Petiole abaxial color*.—Yellow-Green 144B to Greyed-Purple 185C toward base and abscission layer on larger leaves.
*Petiole adaxial surface color*.—Yellow-Green 144B to Greyed-Purple 185C toward base and abscission layer on larger leaves.
*Petiole groove*.—Very shallow, depth 0.1 mm.
*Stipules*.—Present; 10-15 mm length; 1 mm width; color: Yellow-Green 148B.
*Leaf glands*.—None observed.

Leaf buds:
*Length*.—3-5 mm.
*Shape*.—Both lateral and terminal buds pointed with imbricate scales.
*Width*.—2-3 mm.
*Color*.—Yellow-Green 145A with Greyed-Purple 187A overtones.
*Placement on branch*.—Alternate.
*Internode distance*.—20-30 mm.

Spurs: Present on 2 yr and older wood.
*Length*.—Varies from 10 to 200 mm.
*Proportion*.—Proportion means that for every spur that is 100-200 mm in length, there are 2 spurs that are 50-99 mm in length and 7 spurs that are 10-49 mm in length. 100-200 mm=2. 50-100 mm=4. 10-50 mm=14.
*Width*.—3-5 mm.

Flowers at popcorn stage:
*Pedicel*.—Length 13-20 mm; width 2 mm.
*Pedicel color*.—Green Group 138B.
*Bud*.—Length 8 mm; width 10 mm.
*Bud*.—Shape: Both lateral and terminal buds pointed with imbricate scales.
*Bud color*.—Red-Purple 61B.

Flowers at full bloom:
*Bloom time*.—Blooms with 'Golden Delicious' typically during fourth week of April in northern Ohio.
*Bloom period*.—Approximately 7 days.
*Presentation*.—Showy.
*Fragrance*.—Aromatic.
*Fertility*.—Fertile, sheds pollen as petals abscise.
*Number of flowers per cluster*.—4-6 with 5 typical.

Petals:
*Arrangement*.—Bases overlapping; 5 petals per flower; each petal 15-19 mm length, 12-18 mm width.
*Color*.—Upper surface (inside) White Group NN155B; Lower surface (outside) slightly colored, Red-Purple 63A.
*Shape*.—Broadly ovate, almost circular, wide base.
*Veins*.—Distinct, minor lateral veins at base.
*Margins*.—Smooth edge and continuous.
*Texture*.—Soft.
*Receptacle*.—Length 5 mm; width 3 mm; color Green Group 138B with Red-Purple 61A.
*Petal apex*.—Petal apex predominately rounded with some fluting.
*Pedicel*.—Length 15-17 mm; width 2 mm; color Green Group 138B.
*Sepals*.—5/flower; wedge-shaped, sharply pointed; length 5-7 mm; width 4 mm at widest point; adaxial and abaxial color Green Group 138B with Red-Purple 61A.
*Stamens*.—18-20 in number.
*Anthers*.—Length 3 mm; width 2 mm; color Yellow Group 5D.
*Pollen*.—Present and abundant; color Yellow Group 10B.
*Filaments*.—Length 8-9 mm; width 0.5-1 mm; color Green-White 157B.
*Pistil*.—Held above the anthers in majority of blossoms; color Yellow-Green 145B.
*Ovary*.—Length 4 mm; width 3 mm; color Green Group 143C.
*Style*.—Length 10 mm; styles are fused in bottom 3 mm only; width 0.5 mm; color Green Group 145B.
*Stigma*.—Width 0.5 mm; color Green Group 145B.

Pollination requirements: Requires cross-pollination from diploid varieties with overlapping bloom; will pollinate diploid varieties of overlapping bloom.

Fruit:
*Maturity when described*.—3 month storage.
*Date of picking*.—Sep. 2, 2015.
*Size*.—Axial diameter 76-101 mm; Transverse diameter 25-71 mm.
*Fruit weight*.—Average 234 g.
*Form*.—Roundish, oblate.
*Cavity*.—Acuminate, deep, club-shaped stem, russet extends slightly out of cavity.
*Basin*.—Wide, medium, round, not wavy, slightly asymmetrical.
*Calyx*.—Closed, tight.

Skin:
*Thickness*.—Medium.
*Tendency to crack*.—Little.
*Stripes*.—Red, distinct fine stripes, Red Group 46A.

*Lenticels*.—Non-distinct.
*Color*.—Red Group 45A.
*Ground color*.—Yellow-Green 154D.

Flesh:
*Aroma*.—Sweet, mild.
*Locule number per fruit*.—5.
*Color*.—Green-White 157D.
*Texture*.—Crisp, firm, breaking, juicy.
*Eating quality*.—Excellent.

Core: Slightly open.
*Bundle area*.—1190 $mm^2$.
*Bundle*.—Inconspicuous.
*Axial carpel length*.—10-12 mm.
*Seed cells*.—Walls thin, tough.

Seeds:
*Number perfect*.—8-10.
*Number in one cell*.—2.
*Length*.—7-8 mm.
*Breadth*.—4-5 mm.
*Color*.—Greyed-Orange 166B.

Stem:
*Length*.—17-25 mm.
*Width*.—2-3 mm.
*Color*.—Greyed-Yellow 160C.

Use: Fresh market, dessert.
*Fruit brix*.—14-19%.
*Yield*.—Approximately 3.5 bushel/tree at 300 trees/acre=1050 bushels/acre annually.

Shipping quality: Good.
Keeping quality: Good 17 weeks in refrigerated storage.
Drought tolerance: Average for domestic apple.
Tree winter hardiness: Average for domestic apple.

Disease:
*Resistance*.—Slight resistance to fireblight (*Erwinia amylovora*).
*Susceptibility*.—Susceptible to apple scab (*Venturia inaequalis*), powdery mildew (*Podosphaera leucotricha*) and other fungal diseases.

What is claimed is:

1. A new, distinct variety of apple tree named 'MAIA12', as illustrated and described herein.

* * * * *